US008577690B2

(12) United States Patent
Pierce

(10) Patent No.: US 8,577,690 B2
(45) Date of Patent: Nov. 5, 2013

(54) DRUG PRESCRIPTION REGISTRY

(76) Inventor: Dwight L. Pierce, Tulsa, OK (US)

( * ) Notice: Subject to any disclaimer, the term of this patent is extended or adjusted under 35 U.S.C. 154(b) by 1706 days.

(21) Appl. No.: 10/780,166

(22) Filed: Feb. 17, 2004

(65) Prior Publication Data

US 2005/0182662 A1 Aug. 18, 2005

(51) Int. Cl.
*G06Q 50/00* (2012.01)

(52) U.S. Cl.
USPC .................................................. 705/2; 705/3

(58) Field of Classification Search
None
See application file for complete search history.

(56) References Cited

U.S. PATENT DOCUMENTS

| | | | |
|---|---|---|---|
| 5,845,255 A | 12/1998 | Mayaud | |
| 6,263,330 B1 * | 7/2001 | Bessette | 707/4 |
| 6,973,435 B1 * | 12/2005 | Sioufi et al. | 705/2 |
| 7,630,908 B1 * | 12/2009 | Amrien et al. | 705/3 |
| 2002/0194226 A1 * | 12/2002 | Sheth et al. | 707/517 |
| 2003/0050799 A1 | 3/2003 | Jay et al. | |
| 2003/0120513 A1 | 6/2003 | Samaquial | |
| 2003/0154106 A1 | 8/2003 | Marks | |
| 2003/0187692 A1 | 10/2003 | Park | |
| 2003/0236697 A1 * | 12/2003 | Rupp | 705/10 |
| 2004/0006490 A1 * | 1/2004 | Gingrich et al. | 705/2 |
| 2004/0019794 A1 * | 1/2004 | Moradi et al. | 713/185 |

FOREIGN PATENT DOCUMENTS

| | | |
|---|---|---|
| WO | WO 01/09701 A1 | 2/2001 |
| WO | WO 01/37138 A2 | 5/2001 |
| WO | WO 01/37138 A3 | 5/2001 |
| WO | WO 0137138 A2 * | 5/2001 |
| WO | WO 01/86574 A2 | 11/2001 |

* cited by examiner

*Primary Examiner* — Neal Sereboff
*Assistant Examiner* — Anita Coupe
(74) *Attorney, Agent, or Firm* — J. Charles Dougherty

(57) ABSTRACT

Method and system are disclosed for facilitating patient access to pharmacies. The system and method of the present invention involves setting up a prescription registry service. The prescription registry service stores the prescriptions of patients who are members of the registry. Pharmacies, including national and international pharmacies, may then subscribe to the registry service. The pharmacies may be required to satisfy one or more qualification criteria in order to subscribe to the registry service. A patient may then select one of the subscribing pharmacies to fill his prescriptions with reduced risk and increased confidence. Only pharmacies that have been authorized by the patient may access and fill a registered prescription. All communication between the member and the pharmacy are conducted through the pharmacy's normal channels and not through the registry service.

5 Claims, 8 Drawing Sheets

| Field | Value |
|---|---|
| Physician's Name: | |
| Clinic Name: | |
| Patient Given Name: | Allen |
| Patient Second Given Name: | |
| Patient's Surname: | Beaird |
| Shipping Address Line 1: | Address 1 |
| Shipping Address Line 2: | |
| Shipping City: | City |
| Shipping State: | ST |
| Shipping Zip: | 12345 |
| Medication Name: | |
| Generic Name: | |
| Dosage: | |
| Form: | |
| Quantity: | |
| Refills Remaining: | |
| Total Refills: | |
| Date Originally Filled: | |
| Date Last Filled: | |
| Refill Phone Number: | |

Registration Number:

[Click to Register] ~704

(Required entrys are labeled in Bold Text.)

*FIG. 7*

DRUG PRESCRIPTION REGISTRY

FIELD OF THE INVENTION

The present invention relates to healthcare services and, in particular, to a method and system for facilitating patient access to pharmacies.

BACKGROUND OF THE INVENTION

The cost of healthcare in the United States has increased dramatically over the last few years. This increase has affected everyone, whether or not they use the healthcare system. A number of factors contribute to this increase. For example, sprawling suburbs have led to a more sedentary lifestyle, resulting in poorer health overall for the average person. Improvements in medicine and medical technology have extended the average lifespan, resulting in a larger number of senior citizens who, in turn, require more healthcare services.

Once considered a small portion of the overall healthcare cost, prescription drugs are now the fastest growing component of the medical bill. Although new and better drugs are now available for treating many common conditions such as allergies, high cholesterol, and arthritis, these so-called blockbuster drugs are very costly. Also, drug companies are spending more on research, development, and advertising, which fuels the increase in prescription drug cost. Not surprisingly, both individual patients and employer providers of healthcare insurance are looking for options to control prescription drug costs.

One way to control prescription drug cost is through a managed healthcare plan. Examples of managed healthcare plans include health maintenance organizations (HMO), preferred provider organizations (PPO), and other similarly structured healthcare plans. Under these plans, a patient can obtain prescription drugs at a discount, but only if he purchases the drugs from an approved pharmacy. The pharmacies, in turn, agree to charge a lower, prearranged price for the prescription drugs in exchange for being approved. Such an arrangement has obvious benefits for both sides.

A drawback of the above approach, however, is that it is usually available only through employer provided healthcare insurance. The employers, typically a company or corporation, often offset some of the insurance premiums to make them affordable to the employees. Patients who are unemployed and/or self-employed often cannot afford to pay the full premiums for a typical healthcare plan. Also, some patients are precluded from participating in such healthcare plans regardless of their employment due to pre-existing medical conditions.

Moreover, although the prearranged prices charged by pharmacies on the plan are usually lower than pharmacies not on the plan, they are not necessarily the lowest or most competitive prices. For example, lower prices may be obtained from pharmacies in other countries. These foreign pharmacies usually provide the same or substantially the same quality, but routinely sell for up to 50 percent less than the prices charged by pharmacies in the United States. Unfortunately, most people do not have the means to travel to another country to obtain prescription drugs. Additionally, dealing with an unknown foreign pharmacy via postal service or the Internet, without more information, involves considerable risk.

Accordingly, what is needed is an alternative to the prescription drug arrangement of typical healthcare plans. Specifically, a way is needed to expand available prescription drugs supply options beyond the limited number of participating pharmacies currently provided by typical healthcare plans.

SUMMARY OF THE INVENTION

The present invention is directed to a method and system for facilitating patient access to pharmacies. The system and method of the present invention involves setting up a prescription registry service. The prescription registry service stores the prescriptions of patients who are members of the registry. Pharmacies, including national and international pharmacies, may then subscribe to the registry service. The pharmacies may be required to satisfy one or more qualification criteria in order to subscribe to the registry service. A patient may then select one of the subscribing pharmacies to fill his prescriptions with reduced risk and increased confidence. Only pharmacies that have been authorized by the patient may access and fill a registered prescription. All communication between the member and the pharmacy are conducted through the pharmacy's normal channels and not through the registry service.

In general, in one aspect, the invention is directed to a method of facilitating patient access to pharmacies. The method comprises establishing a prescription registry in which patients who have joined the prescription registry may store information regarding their prescriptions, and receiving and storing the information in the prescription registry. The method further comprises assigning a unique prescription identifier to the information for each prescription stored on the prescription registry, the unique prescription identifier initially known only to the patients and the prescription registry. The patients are then provided with a list of pharmacies that have subscribed to the prescription registry, the list including contact information which the patients may use to contact and provide the pharmacies with one or more prescription identifiers. Subscribing pharmacies are then allowed to access the information stored on said prescription registry using the prescription identifiers.

In general, in another aspect, the invention is directed to a system for facilitating patient access to pharmacies. The system comprises a prescription registry, including at least one database for storing prescription information and a user interface for the at least one database. The user interface further comprises a member login screen for allowing a member of the prescription registry to access the at least one database, and a prescription information screen for allowing a member services provider operator to capture prescription information for one or more prescriptions of the member. The user interface further comprises a prescription upload screen for allowing the member services provider operator to upload the prescription information, including a scanned image file of each prescription, to the at least one database, and a prescription verification screen for allowing a pharmacy to access the prescriptions using a unique prescription identifier initially known only to the member and the prescription registry. A prescription acceptance screen allows the pharmacy to accept the one or more prescriptions and lock each prescription that is accepted by the pharmacy from further access.

In general, in yet another aspect, the invention is directed to a prescription registry service. The prescription registry service comprises a database configured to store prescription information, members who upload their prescription information to the database, member services providers that assist the members to upload their prescription information to the database, and pharmacies that access the prescription information stored on the database, wherein the pharmacies are only allowed to access prescription information for which they have been authorized by the members.

BRIEF DESCRIPTION OF THE DRAWINGS

The foregoing and other advantages of the invention will become apparent from the following detailed description and upon reference to the drawings, wherein:

FIG. 7 illustrates an exemplary prescription information screen for a member services provider according to embodiments of the invention;

DESCRIPTION OF ILLUSTRATIVE EMBODIMENTS

Following is a detailed description of illustrative embodiments of the invention with reference to the drawings wherein the same reference labels are used for the same or similar elements. Throughout this description, the term "prescription drug" refers to FDA (Food and Drug Administration) approved medication that requires a prescription from a licensed medical doctor to purchase.

As mentioned above, embodiments of the invention involve setting up a prescription registry service. The prescription registry service provides a cost-effective, confidential, and secure method of procuring prescription drugs from pharmacies other than those typically available through conventional healthcare plans. The prescription registry service allows patients who are members of the service to find pharmacies that have the price and location combination best suited to their individual needs. It is important to note, however, that the prescription registry service does not sell or otherwise distribute the prescription drugs. And although the pharmacies are required to subscribe to the prescription registry service, the service does not directly or indirectly assist the members in the selection of a pharmacy or purchase of the prescription drugs. The prescription registry service merely provides a HIPPA (Health Insurance Portability and Accountability Act) compliant custodial database service to help the members keep a record of their prescriptions. The members may then use their membership accounts to authorize filling of their prescriptions by subscribing pharmacies.

Figure 1:
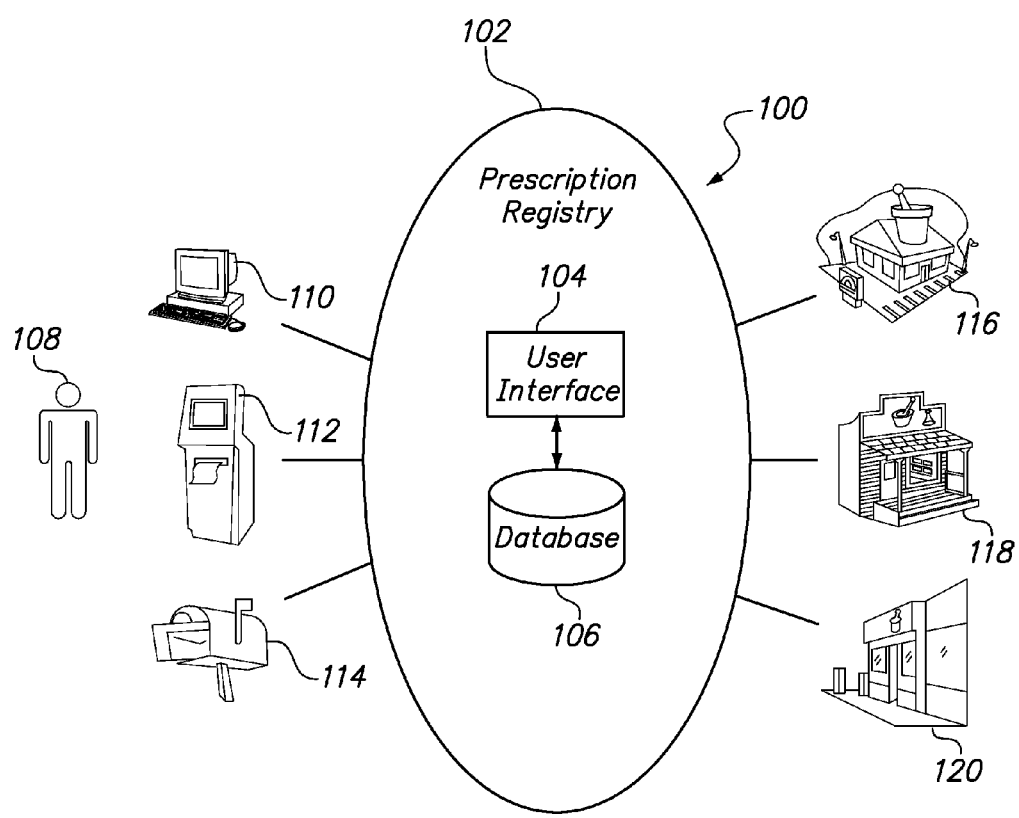
FIG. 1 illustrates an exemplary implementation of a prescription registry service according to embodiments of the invention.

Referring now to FIG. 1, a prescription registry service according to embodiments of the invention is shown generally at 100. The prescription registry service 100 includes a registry 102 that contains, among other things, a user interface 104 and a database 106. The database 106 stores information about the members of the prescription registry service 100 (e.g., name, date of birth, contact information, etc.) as well as the particulars of their prescriptions (e.g., physician, drug name, dosage, number of refills, etc.). In some embodiments, the database 106 also stores information about the pharmacies that have subscribed to the prescription registry service 100. Access to the database 106 is provided through the user interface 104. The user interface 104 allows the members, the subscribing pharmacies, and anyone else who may need to view and/or or modify the information in the database 106 to do so in a graphical, user-friendly, and intuitive manner.

In a preferred embodiment, the registry 102 may be implemented as a Web based application that it is accessible from the Internet using any commercially available Web browser. It is possible, however, to implement the registry 102 using some other public or a private network without departing from the scope of the invention. In addition, although only a single database 106 is shown in FIG. 1, a person having ordinary skill in the art will understand that multiple databases may be used as needed without departing from the scope of the invention. For example, in some embodiments, a separate database may be used for the member information, the subscribing pharmacies information, the prescription information, and other information.

Patients who are members (shown generally at 108) of the prescription registry service 100 may register their prescriptions on the registry 102. They may do this on their own or they may have a third party register the prescriptions on their behalf. To register the prescriptions themselves, the members 108 may simply access the registry 102 using a personal computing device 110, such as a desktop computer, laptop computer, personal digital assistant (PDA), and the like. Alternatively, the members 108 may register their prescriptions using one of several conveniently located member services providers (MSP) 112 that have been specifically designed and equipped to access the registry 102. The members 108 may also mail their prescriptions to the registry 102, or more precisely, to the administrator of the registry 102, via any suitable postal service 114 and let the administrator handle the registration.

To complete the registrations, the members 108 must surrender their original prescription slips to the registry administrator. This step is important in order to help prevent situations where a single prescription is filled multiple times. Thus, if a member 108 is registering his own prescriptions, he must mail the original prescription slips to the registry administrator. If the member 108 is using an MSP 112 to register his prescriptions, he must surrender the original prescription slips to the MSP operator, who will then mail the original prescription slips to the registry administrator. Alternatively, instead of giving the original prescription slips to the MSP operator, the member 108 may place the slips in a secure drop box attached to the MSP 112 where they will be subsequently picked up and mailed to the registry administrator. In any case, only after the administrator of the registry 102 has obtained physical possession of the original prescription slips will the prescriptions be made accessible on the registry 102.

Once the prescriptions have been registered, the members 108 may authorize one of the pharmacies (indicated generally at 116-120) that have subscribed to the prescription registry service 100 to fill their prescriptions. The members 108 may do this by selecting the pharmacies from a list of subscribing pharmacies 116-120 stored in the database 106 of the registry 102. The list preferably includes the names of the pharmacies as well as their contact information (e.g., address, telephone number, fax number, email address, Web URL, etc.). The members 108 may then contact one of the pharmacies and provide them with identifying information that may be used to access the prescriptions stored in the registry 102. No pharmacy may access any of the prescriptions on the registry 102 unless the pharmacy provides the registry with the prescription identifying information.

Note that other than providing the contact information, the registry 102 does not facilitate any communication between the members 108 and the pharmacies 116-120. All communications and transactions between the members 108 and the pharmacies 116-120, including transfers of prescription identifying information and delivery of prescription drugs, take place through the pharmacies' normal channels (e.g., telephone, fax, email, postal service, etc.) and not through the prescription registry service 100.

An advantage of the prescription registry service 100 is that any pharmacy, including international pharmacies, may subscribe to the prescription registry service. As mentioned previously, many foreign pharmacies sell prescription drugs that have the same or substantially the same quality as their counterparts in the United States, but at a significant discount. With the prescription registry service 100, the members 108 now have the flexibility of filling their prescriptions using one of these foreign pharmacies without having to travel to another country.

To provide a measure of protection for the members 108, in a preferred embodiment, all pharmacies 116-120 are required to satisfy one or more qualification criteria, such as passing a background check, before they can subscribe to the prescription registry service 100. Typically, the pharmacy must be legally licensed to dispense prescription drugs in its home country, must have been in business continuously for at least the last 12 months, and must not have more than a predetermined amount (e.g., 1%) of unresolved customer complaints. Such an arrangement helps ensure that the subscribing pharmacies 116-120 meet a minimum level of quality and reliability in their dealings.

Further, in some embodiments, the subscribing pharmacies 116-120 may be required to certify their good standing from time to time in order to maintain their subscriptions. In other embodiments, a member complaint system may be implemented to track member complaints against the pharmacies. For example, a pharmacy may have its subscription suspended or terminated after a certain number of member complaints have been lodged about that pharmacy.

As part of their subscription, the pharmacies 116-120 may be required to pay a fee to the administrator of the registry 102. The fee may be a periodically recurring subscription fee (e.g., monthly, quarterly, annually, etc.), or it may be a transaction based fee (e.g., a fixed amount for each prescription filled, a percentage of each prescription filled, etc.). A similar subscription or transaction based fee arrangement may be charged for MSPs 112 that are owned and operated independently of the prescription registry service 100. No fee is contemplated for MSPs 112 that are owned and operated by the prescription registry service 100 itself. Other fee arrangements may also be used, such as those involving a free trial period, without departing from the scope of the invention. In some embodiments, the members 108 may also be charged a minimal membership or transaction-based fee in order to be members of the prescription registry service 100.

As part of their membership, the members 108 have access to several member related resources. For example, in addition to registering and filling their prescriptions, the members may also update their membership information, view their open prescriptions, search for MSP locations, and the like. These tasks may be performed using the user interface 104 mentioned above. Other parties may also use the user interface 104 to access the registry 102 as needed. For example, subscribing pharmacies 116-120 may use the user interface 104 to view the registered prescriptions, the MSPs operators may use the user interface 104 to register the prescriptions, and so on. Following is a description of one exemplary implementation of the user interface 104.

Figure 2:
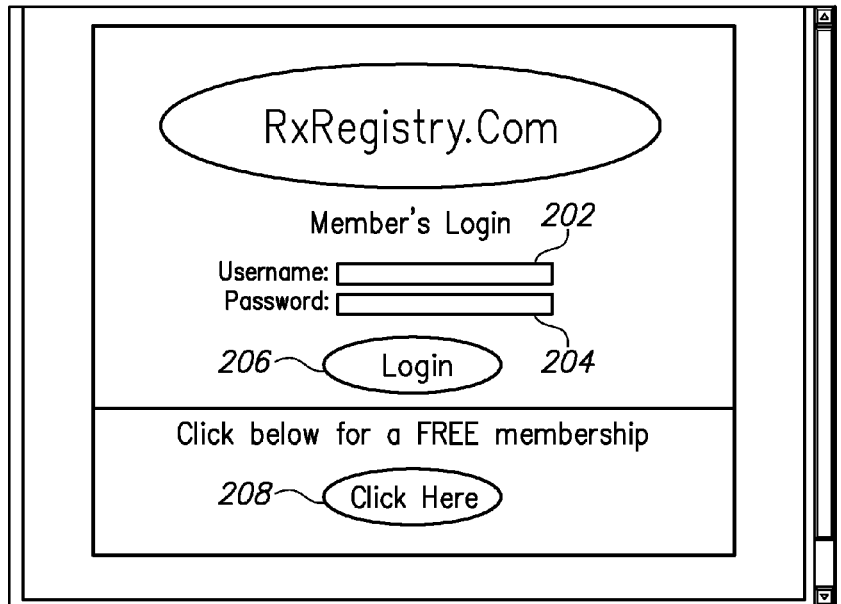
FIG. 2 illustrates an exemplary member login screen according to embodiments of the invention.

Referring now to FIG. 2, in some embodiments, the user interface 104 may include a member login screen, an example of which is shown at 200. The members login screen 200 preferably includes a username field 202 and a password field 204 for existing members to enter their usernames and passwords. A login button 206 lets the members log in to their membership accounts after providing their usernames and passwords. For patients who are not members, a new member button 208 leads to a membership application screen, an example of which is shown at 300 in FIG. 3.

Figure 3:
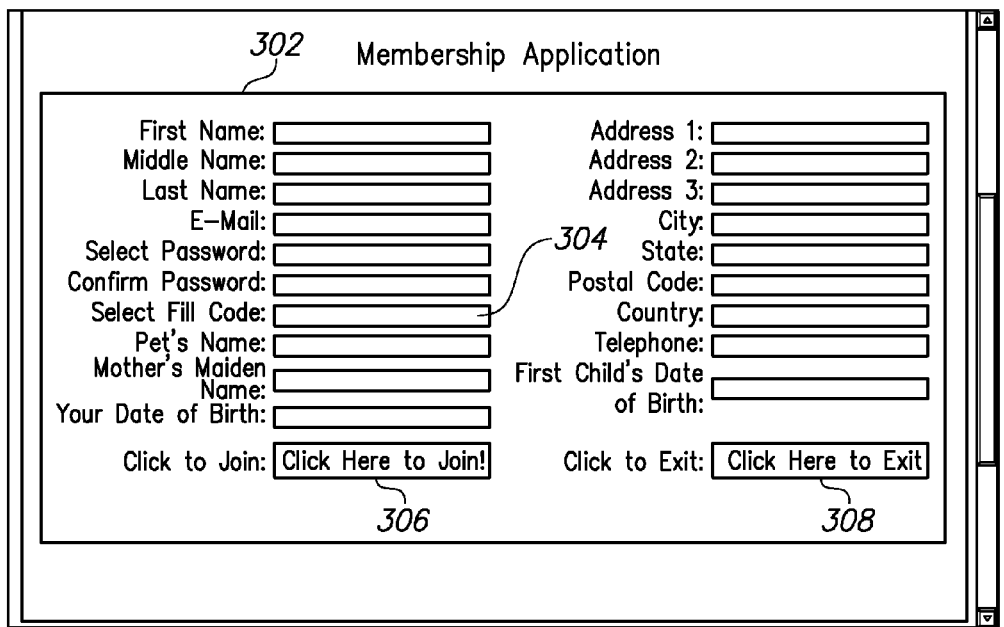
FIG. 3 illustrates an exemplary membership application screen according to embodiments of the invention.

As can be seen in FIG. 3, the membership application screen 300 includes an application form 302, preferably one that is HIPAA compliant that contains a plurality of fields for entering personal information about the patients. The personal information may include, for example, the patients' names, addresses, telephone numbers, passwords, and the like. In some embodiments, the patient may also select their fill codes (indicated at 304), which are strings of alpha and/or numeric characters that will subsequently be used by the pharmacies to access the patients' prescriptions. In other embodiments, however, the fill codes 304 may be generated automatically for the patients by the registry. In either case, in a preferred embodiment, no pharmacy may access any prescription in the registry without the fill code 304 for that prescription. Finally, buttons 306 and 308 allow the membership application form 302 to be submitted or canceled, respectively.

Figures 4, 5:
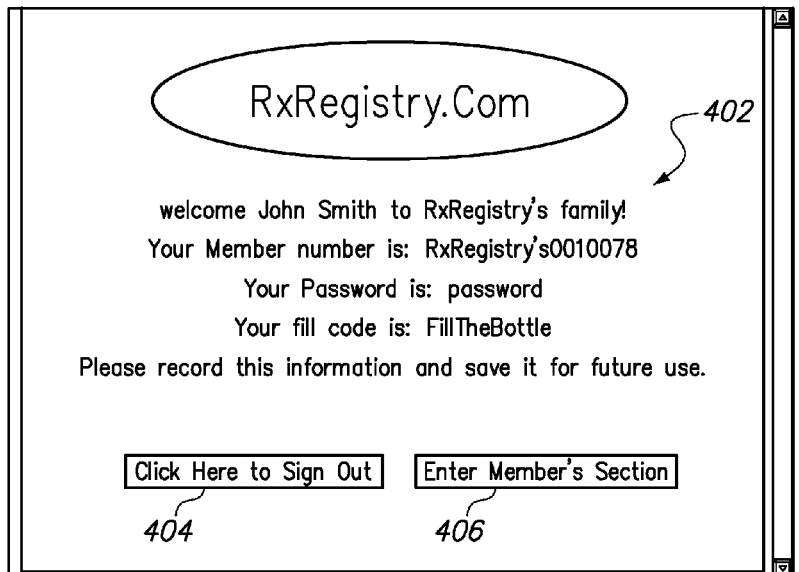
FIG. 4 illustrates an exemplary membership confirmation screen according to embodiments of the invention.
FIG. 5 illustrates an exemplary membership services screen according to embodiments of the invention.

Upon submission of the membership application form, the user interface 104 returns a membership confirmation screen, an example of which is shown at 400 in FIG. 4. The membership confirmation screen 400 provides the new members with their membership information (shown generally at 402), including their member user numbers, passwords, and fill codes. In some embodiments, the new members may be required to read and accept a predefined registry membership agreement before the user interface 104 presents the membership confirmation screen 400. The members may thereafter register their prescriptions and authorize one or more subscribing pharmacies to fill the prescriptions.

In some embodiments, the same fill code may be used for all the prescriptions of a particular member. In that case, each prescription for a particular member may be individually enumerated at the time the prescription is registered such that any prescription may be uniquely identified using the combination of the fill code and the prescription number. It is also possible, however, to have a separate fill code for each prescription and no enumeration, or some other combination of the above. Buttons 404 and 406 allow the members to log out of the registry or to continue on to the member services portion of the registry, respectively.

If the member chooses to continue on to the member services portion of the registry, the user interface 104 presents the members with a member services screen, an example of which is shown at 500 in FIG. 5. The member services screen 500 includes a plurality of option tabs that let the members use various services available to them. For example, an update account tab 502 lets the members update membership information, such as their names, addresses, telephone numbers, passwords, fill codes, and the like. A logoff tab 504 allows the members to exit the registry. A locate tab 506 allows the members to view a list 508 of participating MSPs and a list 510 of subscribing pharmacies. The lists 508 and 510 preferably include enough information (e.g., names, addresses, telephone numbers, etc.) about the MSPs and the pharmacies to allow the members to contact these entities.

In some embodiments, in addition to contact information, the list 510 of pharmacies may also provide information regarding the prescription drugs available from the pharmacies along with pricing information. For example, each entry in the list 510 of pharmacies may include a hyperlink to a chart or table that contains drug availability and pricing information for that pharmacy. Alternatively, the list 510 of pharmacies may include hyperlinks to the Web URL of the pharmacies where the members may obtain such information. The list 508 of MSP may also include hyperlinks to information about the MSP, such as a map showing the location of the MSP and/or driving instructions.

To register their prescriptions through an MSP, the members may take their prescriptions to one of the MSPs in the list 508. The MSPs, as mentioned above, are customized and equipped with the necessary equipment to access the registry. Further, each MSP operator has been given a username and password under a predefined MSP agreement with the registry administrator for logging into the registry. The MSP operators may then log in to the registry from the MSP using any commercially available Web browser. The login screen for the MSP operators is similar to the login screen of the members (see FIG. 2) and, therefore, will not be described here.

Figure 6:
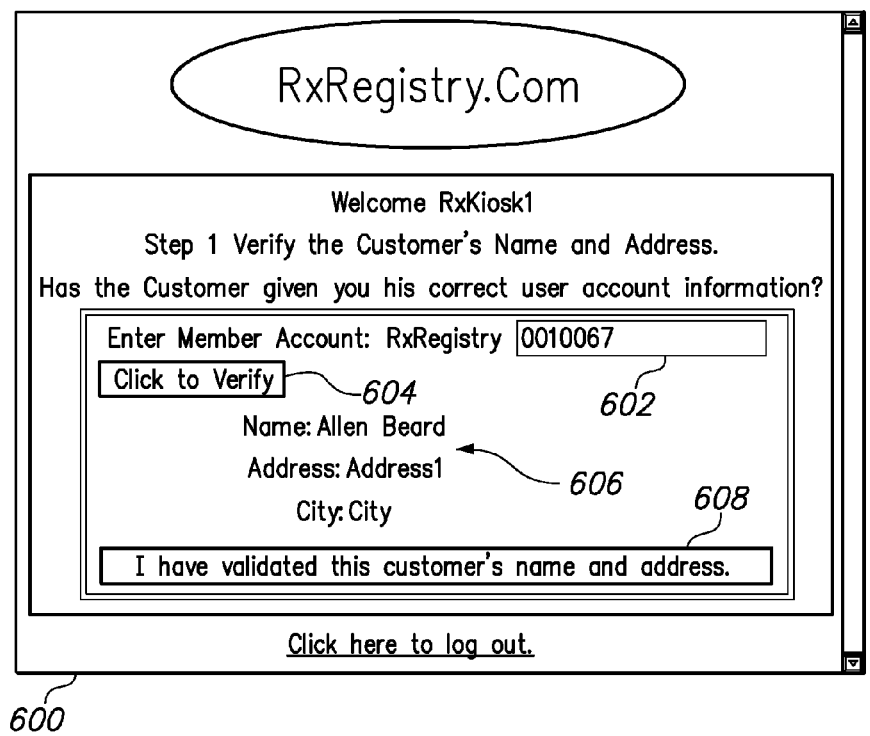
FIG. 6 illustrates an exemplary membership verification screen for a member services provider according to embodiments of the invention.

Once logged in, the MSP operators are presented with a member confirmation screen, an example of which is shown at 600 in FIG. 6. The member confirmation screen 600 includes a username field 602 for the MSP operators to enter the members' usernames or user numbers. A verify button 604 allows the MSP operators to pull the membership information corresponding to the entered usernames or user numbers from the registry database. The MSP operators may then compare the membership information on the confirmation screen 600 with a driver's license, social security card, or some other form of identification from the members. If the MSP operators are satisfied with the identity of the members, they may press a validation button 608 to validate the members.

Successful validation of the members leads to a prescription registration screen, an example of which is shown at 700 in FIG. 7. The prescription registration screen 700 includes a prescription registration form 702 for filling in the members' prescription information. The prescription registration form 702 contains a plurality of fields for entering various items of information related to the prescriptions, such as the physician's name, clinic name, the name of the medication, number of refills, and the like. Some of these fields, such as the personal information fields (e.g. names, addresses, etc.), may be pre-filled with information from the membership account contained in the registry database. After all necessary fields have been completed, a register button 704 allows the MSP operator to upload the members' prescriptions to the registry.

Figure 8:
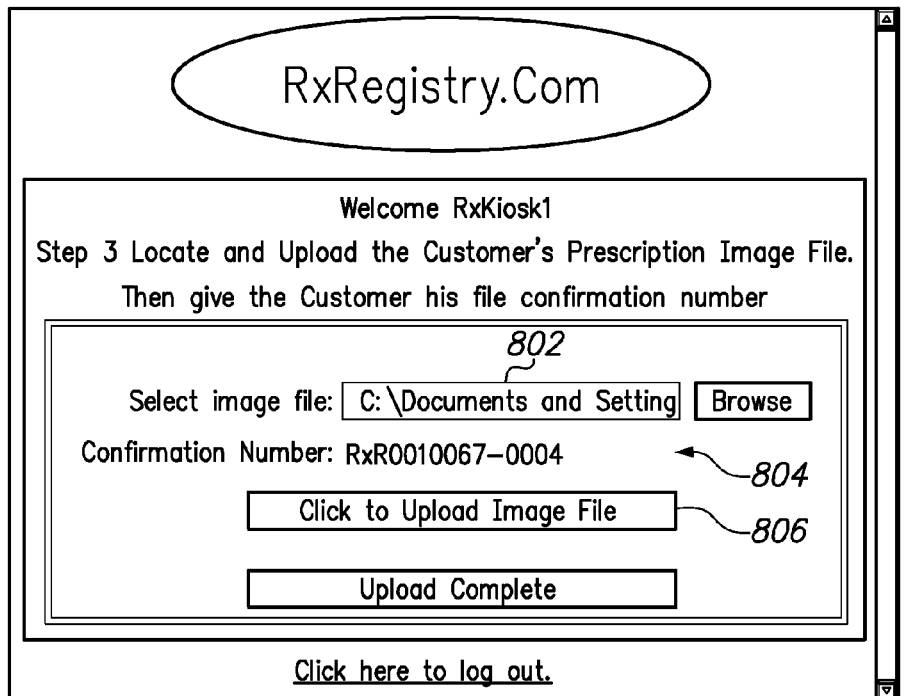
FIG. 8 illustrates an exemplary prescription upload screen for a member services provider according to embodiments of the invention.

In addition to the prescription registration form 702, the MSP operators also scan the prescriptions into image files (using a suitable scanner) and upload the image files to the registry 102. FIG. 8 illustrates an example of an image file screen 800 that can be used to upload image files to the registry. The image file screen 800 contains an image file field 802 that includes a browse function for allowing the MSP operators to locate the image files for the prescriptions. The image file screen 800 also includes an enumeration function that assigns a unique prescription number to each prescription and image file of a particular member. The prescription number may be assigned sequentially, pseudo-randomly, or according to some other predefined algorithm. In some embodiments, the combination of the members' usernames or user numbers and the prescription numbers may be used as a confirmation number, as shown at 804. An upload button 806 allows the MSP operators to upload the image files to the registry.

To complete the registration process, the MSP operator may take physical possession of the original prescriptions slips from the members, or the members may deposit the original prescriptions slips in a secure drop box. For MSPs that are not manned, the members may simply deposit the original prescriptions slips in a secure drop box without filling in any forms or scanning any prescription slips. Thereafter, a designated courier may be assigned to pick up the prescriptions slips and deliver them to the administrator of the registry to complete the registrations.

In some embodiments, instead of going to an MSP, the members may register their own prescriptions by logging into the registry from their home computers. From there, the members may complete a prescription registration form similar to the prescription form 702 shown in FIG. 7. The members may then scan the prescription slips (using a suitable scanner), upload the image files, and mail the original prescription slips to the administrator of the registry.

After the prescriptions have been registered, the members may authorize one of the subscribing pharmacies to fill the prescriptions by providing the pharmacies with the members' fill codes and the prescription numbers for the prescriptions to be filled. With this information, the pharmacies may log in to the registry and access the information for the prescriptions. Each subscribing pharmacy has been given a username and password under a predefined subscriber agreement with the registry administrator that may be used to log in to the registry. The login screen for the pharmacies is similar to the login screen for the members (see FIG. 2) and, therefore, will not be described here.

Figure 9:
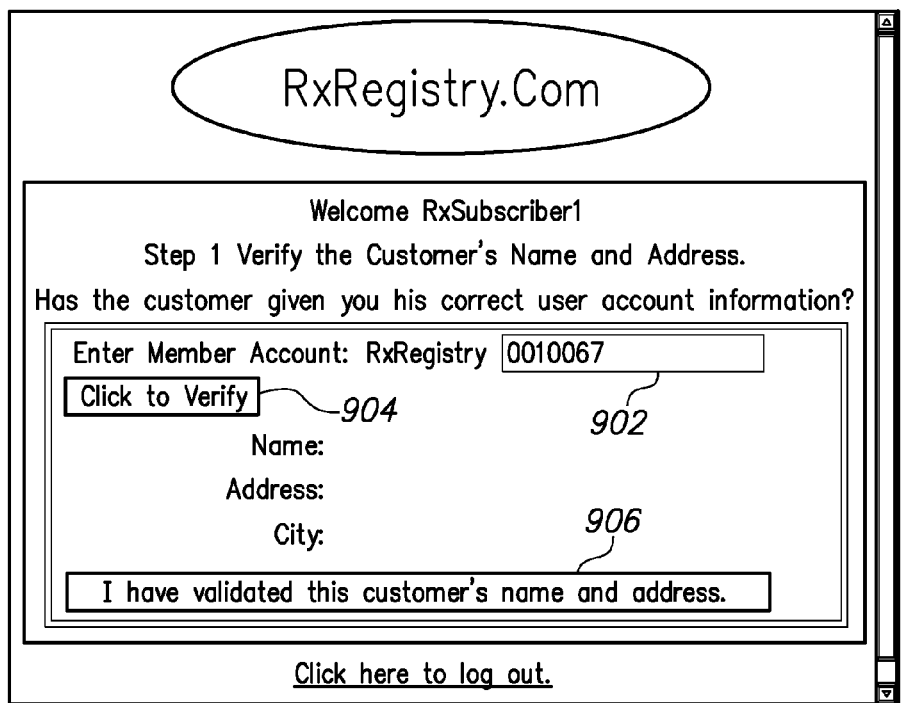
FIG. 9 illustrates an exemplary membership verification screen for a pharmacy according to embodiments of the invention.

Upon logging in, the pharmacies are presented with a member confirmation screen, an example of which is shown at 900 in FIG. 9. The member confirmation screen 900 is similar to the member confirmation screen 600 shown in FIG. 6 in that it includes a username field 902 for entering the members' usernames or user numbers. A verify button 904 allows the pharmacies to pull up the membership information corresponding to the entered usernames or user numbers from the registry database. The pharmacies may then compare the membership information on the confirmation screen 900 with identifying information provided by the members. If the pharmacies are satisfied with the identity of the members, they may press a validation button 906 to validate the members.

Figure 10:
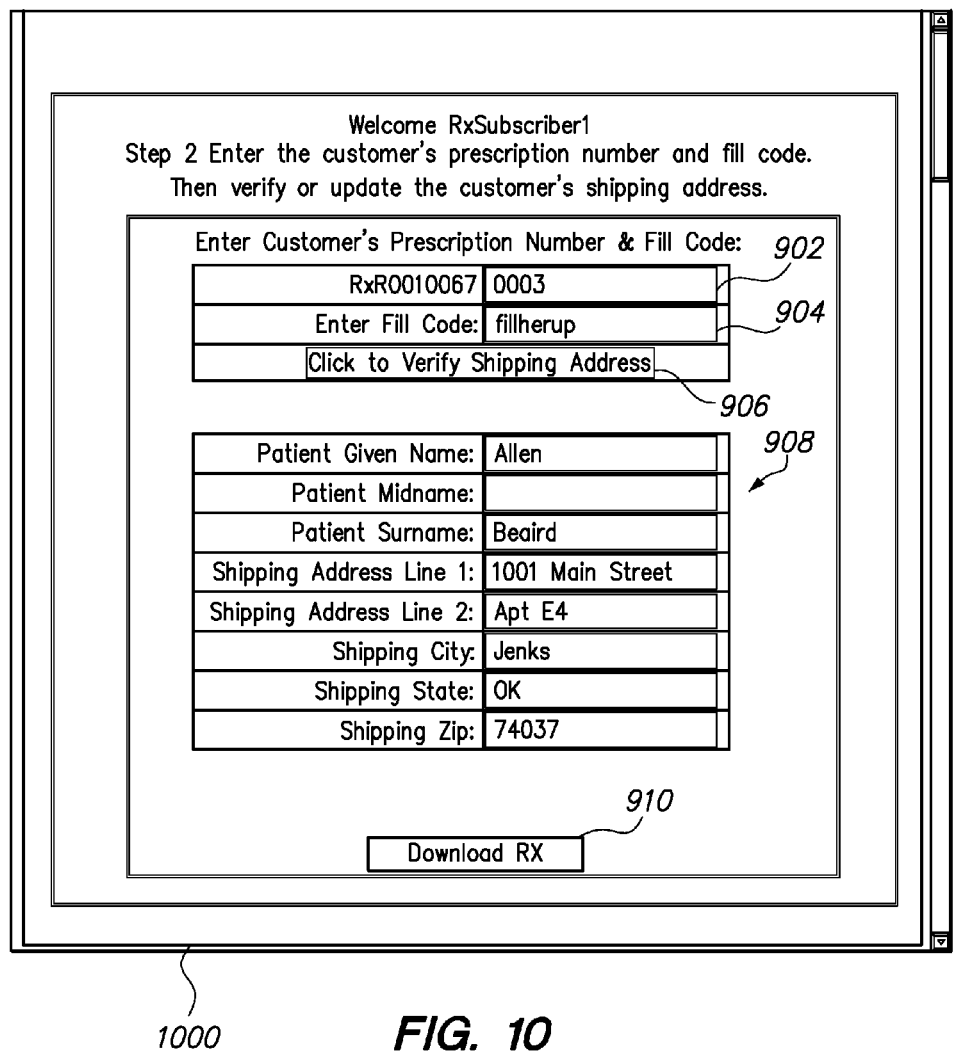
FIG. 10 illustrates an exemplary prescription verification screen for a pharmacy according to embodiments of the invention.

After validation of the members, the pharmacies are presented with a prescription verification screen, an example of which is shown at 1000 in FIG. 10. The prescription verification screen 1000 may include a prescription number field 1002 and a fill code field 1004 for entering the prescription numbers and the fill codes provided by the members. The combination of prescription number and fill code allows the pharmacies to uniquely identify a particular prescription to be filled. A verify shipping address button 1006 obtains the members' names and shipping address information (shown generally at 1008) from the registry database. If the pharmacies are satisfied that the shipping address information is correct, they may press a download prescription button 1010 to access the prescriptions to be filled.

Figure 11:
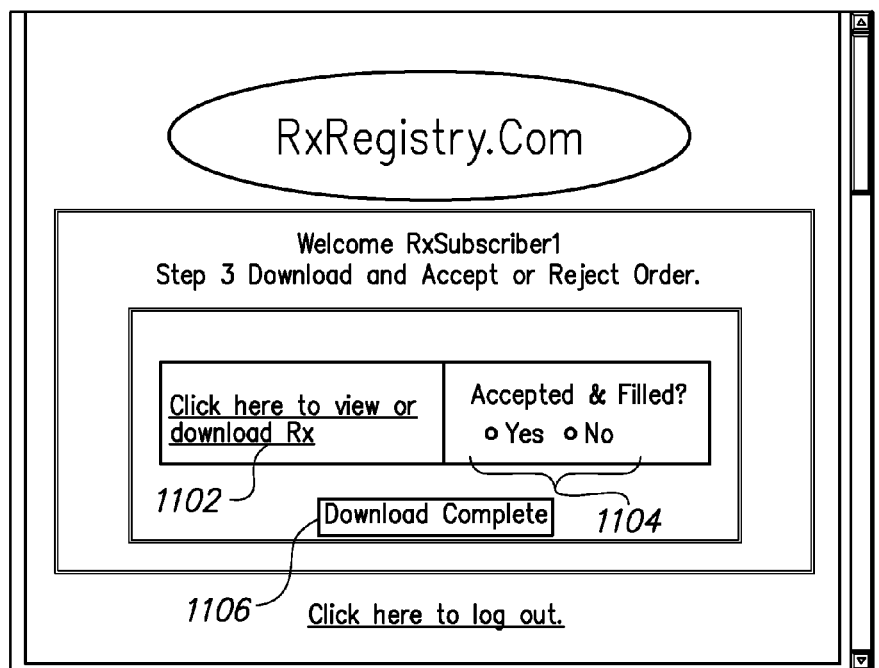
FIG. 11 illustrates an exemplary prescription acceptance screen for a pharmacy according to embodiments of the invention.

Accessing the prescriptions to be filled may be accomplished through a prescription acceptance screen, an example of which is shown at 1100 in FIG. 11. The prescription acceptance screen 1100 may include a hyperlink to either the image files of the prescriptions to be filled or the prescription registration forms therefor (see FIG. 7), or both. The pharmacies may thereafter download the information to their computers or they may view them online if they so choose, or both. In any case, the pharmacies can now view all the information necessary to fill the prescriptions. Radio buttons 1104 allow the pharmacies to either accept or decline the prescriptions. Acceptance of the prescriptions causes the registry database to close and lock the accepted prescriptions so that no other pharmacies can access or view them. As mentioned previously, this feature helps prevent situations where a single prescription is filled more than one time. Pressing a complete button 1106 returns the pharmacies to the prescription verification screen 1000, where the pharmacies may continue to view other authorized prescriptions or they may exit the registry.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. A method of facilitating patient access to pharmacies, comprising:
    establishing in a database on a computer server a prescription registry in which patients who have joined said prescription registry may store information regarding their prescriptions, wherein said information comprises an alphanumeric fill code associated with each of said prescriptions for each said patient wherein said fill code for each of said patients is chosen by that one of said patients;
    transmitting said information from a member device to said computer server over a computer network connecting the member device and the computer server;
    receiving and storing said information in said prescription registry on said computer server;
    assigning by said computer server a prescription identifier to said information, wherein each prescription identifier is uniquely associated with an individual prescription within said prescription registry, and storing said prescription identifier in a record associated with such prescription in said database on said computer server, said prescription identifier initially known only to said patients and said prescription registry;
    receiving at the computer server qualification information from a plurality of pharmacies;
    comparing the qualification information against at least one qualification criteria, wherein the at least one qualification criteria comprises (i) being established in business for at least twelve months or (ii) not having more than a pre-determined number of unresolved customer complaints;
    preparing at the computer server a list of pharmacies meeting the at least one qualification criteria established at the computer server, wherein the list is comprised of contact information for the qualified pharmacies;
    transmitting from said computer server to said member device the list of pharmacies that have subscribed to said prescription registry;
    transmitting from said member device to a pharmacy device associated with one of the list of pharmacies a fill request message, wherein the fill request message comprises said prescription identifier and said fill code, and further wherein the fill request message is not transmitted to said computer server;
    transmitting a prescription request from a pharmacy device to said computer server, wherein said prescription request comprises said prescription identifier assigned to said prescription and said fill code chosen by said patient;
    searching said prescription registry for said record containing said prescription identifier and said fill code received from said pharmacy device;
    transmitting said prescription associated with said prescription identifier and said fill code from said prescription registry on said computer server to said pharmacy device whereby the pharmacy associated with said pharmacy device may fill the prescription; and
    locking said record containing said prescription identifier and said fill code such that a different pharmacy may not receive and fill said prescription associated with said record from said prescription registry even if said different pharmacy possesses said prescription identifier and said fill code.

2. The method according to claim 1, wherein said step of receiving said information includes receiving from said member device a scanned image file at said computer server of an original prescription slip for each prescription.

3. The method according to claim 2, wherein said step of receiving said information further includes obtaining physical possession of an original prescription slip for each prescription.

4. The method according to claim 1, further comprising requiring said pharmacies to satisfy one or more qualification criteria, including passing a background check, in order to subscribe to said prescription registry.

5. The method according to claim 1, further comprising requiring said subscribing pharmacies to pay a fee to said prescription registry.

* * * * *